US010207069B2

(12) United States Patent
Jafari et al.

(10) Patent No.: US 10,207,069 B2
(45) Date of Patent: Feb. 19, 2019

(54) SYSTEM AND METHOD FOR DETERMINING VENTILATOR LEAKAGE DURING STABLE PERIODS WITHIN A BREATH

(75) Inventors: Mehdi M. Jafari, Laguna Hills, CA (US); Rhomere S. Jimenez, Winchester, CA (US); Jeffrey K. Aviano, Escondido, CA (US); Gail F. Upham, Fallbrook, CA (US)

(73) Assignee: Covidien LP, Mansfield, MA (US)

( * ) Notice: Subject to any disclaimer, the term of this patent is extended or adjusted under 35 U.S.C. 154(b) by 1589 days.

(21) Appl. No.: 13/059,711

(22) PCT Filed: Mar. 30, 2009

(86) PCT No.: PCT/US2009/038819
§ 371 (c)(1),
(2), (4) Date: Jul. 8, 2011

(87) PCT Pub. No.: WO2009/123980
PCT Pub. Date: Oct. 8, 2009

(65) Prior Publication Data
US 2011/0259330 A1    Oct. 27, 2011

Related U.S. Application Data

(60) Provisional application No. 61/041,070, filed on Mar. 31, 2008, provisional application No. 61/122,288, filed on Dec. 12, 2008.

(51) Int. Cl.
*A61M 16/00* (2006.01)

(52) U.S. Cl.
CPC ....... *A61M 16/024* (2017.08); *A61M 16/0063* (2014.02); *A61M 2016/0021* (2013.01);
(Continued)

(58) Field of Classification Search
CPC .. A61M 16/00–16/0012; A61M 16/02; A61M 16/04; A61M 16/0402;
(Continued)

(56) References Cited

U.S. PATENT DOCUMENTS 3,805,780 A    4/1974 Cramer et al.
3,941,124 A    3/1976 Rodewald et al.
(Continued)

FOREIGN PATENT DOCUMENTS

DE    19808543 A1    11/1998
EP    0425092 A    5/1991
(Continued)

OTHER PUBLICATIONS

Jafari, M. et al., "Robust Feedback Design for Proportional Assist Ventilation-System Dynamics and Problem Definition" Decision and Control, 2005 and 2005 European Control Conference. CDC-E CC '05. 44TH IEEE Conference on Seville, Spain Dec. 12-15, 2005 (Dec. 12, 2005), pp. 4839-4844, XP010884460 DISBN: 978-0-7803-9567-1, the whole document.
(Continued)

*Primary Examiner* — Gregory Anderson
*Assistant Examiner* — Ned T Heffner
(74) *Attorney, Agent, or Firm* — Merchant & Gould P.C.

(57) ABSTRACT

Systems and methods for compensating for leaks in a ventilation system based on data obtained during periods within a breath in which the patient is neither inhaling nor exhaling. The methods and systems described herein more accurately and quickly identify changes in leakage. This information is then to estimate leakage later in the same breath or in subsequent breaths to calculate a more accurate estimate of instantaneous leakage based on current conditions. The estimated leakage is then used to compensate for the leak flow rates, reduce the patient's work of breathing
(Continued)

and increase the patient's comfort (patient-ventilator breath phase transition synchrony).

22 Claims, 4 Drawing Sheets

(52) U.S. Cl.
CPC .............. *A61M 2016/0027* (2013.01); *A61M 2016/0033* (2013.01); *A61M 2205/15* (2013.01); *A61M 2205/50* (2013.01); *A61M 2205/505* (2013.01); *A61M 2230/46* (2013.01)

(58) Field of Classification Search
CPC .......... A61M 16/0427; A61M 16/0434; A61M 16/044; A61M 16/0096; A61M 16/06–16/0666; A61M 16/0045–16/0084; A61M 2016/0015–2016/0042
See application file for complete search history.

(56) References Cited

U.S. PATENT DOCUMENTS

| | | | |
|---|---|---|---|
| 4,056,098 A | 11/1977 | Michel et al. | |
| 4,305,388 A | 12/1981 | Brisson | |
| 4,340,044 A | 7/1982 | Levy et al. | |
| 4,448,192 A | 5/1984 | Stawitcke et al. | |
| 4,752,089 A | 6/1988 | Carter | |
| 4,766,894 A | 8/1988 | Legrand et al. | |
| 4,921,642 A | 5/1990 | LaTorraca | |
| 4,939,647 A | 7/1990 | Clough et al. | |
| 4,954,799 A | 9/1990 | Kumar | |
| 4,971,052 A | 11/1990 | Edwards | |
| 4,972,842 A | 11/1990 | Korten et al. | |
| 4,986,268 A | 1/1991 | Tehrani | |
| 5,057,822 A | 10/1991 | Hoffman | |
| 5,065,350 A * | 11/1991 | Fedder ............. | 702/98 |
| 5,072,728 A | 12/1991 | Pasternack | |
| 5,072,737 A | 12/1991 | Goulding | |
| 5,094,235 A | 3/1992 | Westenskow et al. | |
| 5,148,802 A | 9/1992 | Sanders et al. | |
| 5,150,291 A | 9/1992 | Cummings et al. | |
| 5,161,525 A | 11/1992 | Kimm et al. | |
| 5,237,987 A | 8/1993 | Anderson et al. | |
| 5,239,995 A | 8/1993 | Estes et al. | |
| 5,259,373 A | 11/1993 | Gruenke et al. | |
| 5,271,389 A | 12/1993 | Isaza et al. | |
| 5,279,549 A | 1/1994 | Ranford | |
| 5,299,568 A | 4/1994 | Forare et al. | |
| 5,301,921 A | 4/1994 | Kumar | |
| 5,313,937 A | 5/1994 | Zdrojkowski et al. | |
| 5,315,989 A | 5/1994 | Tobia | |
| 5,316,009 A | 5/1994 | Yamada | |
| 5,319,540 A | 6/1994 | Isaza et al. | |
| 5,325,861 A | 7/1994 | Goulding | |
| 5,333,606 A | 8/1994 | Schneider et al. | |
| 5,339,807 A | 8/1994 | Carter | |
| 5,343,857 A | 9/1994 | Schneider et al. | |
| 5,351,522 A | 10/1994 | Lura | |
| 5,357,946 A | 10/1994 | Kee et al. | |
| 5,365,922 A | 11/1994 | Raemer | |
| 5,368,019 A | 11/1994 | LaTorraca | |
| 5,383,449 A | 1/1995 | Forare et al. | |
| 5,385,142 A | 1/1995 | Brady et al. | |
| 5,388,575 A | 2/1995 | Taube | |
| 5,390,666 A | 2/1995 | Kimm et al. | |
| 5,398,682 A | 3/1995 | Lynn | |
| 5,401,135 A | 3/1995 | Stoen et al. | |
| 5,402,796 A | 4/1995 | Packer et al. | |
| 5,407,174 A | 4/1995 | Kumar | |
| 5,413,110 A | 5/1995 | Cummings et al. | |
| 5,429,123 A | 7/1995 | Shaffer et al. | |
| 5,433,193 A | 7/1995 | Sanders et al. | |
| 5,438,980 A | 8/1995 | Phillips | |
| 5,443,075 A | 8/1995 | Holscher | |
| 5,492,113 A | 2/1996 | Estes et al. | |
| 5,503,146 A | 4/1996 | Froehlich et al. | |
| 5,503,147 A | 4/1996 | Bertheau | |
| 5,513,631 A | 5/1996 | McWilliams | |
| 5,517,983 A | 5/1996 | Deighan et al. | |
| 5,520,071 A | 5/1996 | Jones | |
| 5,524,615 A | 6/1996 | Power | |
| 5,531,221 A | 7/1996 | Power | |
| 5,535,738 A | 7/1996 | Estes et al. | |
| 5,540,220 A | 7/1996 | Gropper et al. | |
| 5,542,415 A | 8/1996 | Brady | |
| 5,544,674 A | 8/1996 | Kelly | |
| 5,549,106 A | 8/1996 | Gruenke et al. | |
| 5,551,418 A | 9/1996 | Estes et al. | |
| 5,551,419 A | 9/1996 | Froehlich et al. | |
| 5,555,880 A | 9/1996 | Winter et al. | |
| 5,596,984 A | 1/1997 | O'Mahony et al. | |
| 5,598,838 A | 2/1997 | Servidio et al. | |
| 5,605,151 A | 2/1997 | Lynn | |
| 5,623,923 A | 4/1997 | Bertheau et al. | |
| 5,630,411 A | 5/1997 | Holscher | |
| 5,632,269 A | 5/1997 | Zdrojkowski | |
| 5,632,270 A | 5/1997 | O'Mahony et al. | |
| 5,645,048 A | 7/1997 | Brodsky et al. | |
| 5,645,053 A | 7/1997 | Remmers et al. | |
| 5,650,943 A * | 7/1997 | Powell et al. ............. | 702/51 |
| 5,660,171 A | 8/1997 | Kimm et al. | |
| 5,664,560 A | 9/1997 | Merrick et al. | |
| 5,664,562 A | 9/1997 | Bourdon | |
| 5,671,767 A | 9/1997 | Kelly | |
| 5,672,041 A | 9/1997 | Ringdahl et al. | |
| 5,673,689 A | 10/1997 | Power | |
| 5,685,296 A | 11/1997 | Zdrojkowski et al. | |
| 5,687,715 A | 11/1997 | Landis et al. | |
| 5,692,497 A | 12/1997 | Schnitzer et al. | |
| 5,715,812 A | 2/1998 | Deighan et al. | |
| 5,719,785 A * | 2/1998 | Standifer ............. | 702/51 |
| 5,752,509 A | 5/1998 | Lachmann et al. | |
| 5,762,480 A | 6/1998 | Adahan | |
| 5,771,884 A | 6/1998 | Yarnall et al. | |
| 5,791,339 A | 8/1998 | Winter | |
| 5,794,615 A | 8/1998 | Estes | |
| 5,794,986 A | 8/1998 | Gansel et al. | |
| 5,803,065 A | 9/1998 | Zdrojkowski et al. | |
| 5,813,399 A | 9/1998 | Isaza et al. | |
| 5,823,187 A | 10/1998 | Estes et al. | |
| 5,826,575 A | 10/1998 | Lall | |
| 5,829,441 A | 11/1998 | Kidd et al. | |
| 5,864,938 A | 2/1999 | Gansel et al. | |
| 5,865,168 A | 2/1999 | Isaza | |
| 5,876,352 A | 3/1999 | Weismann | |
| 5,881,717 A | 3/1999 | Isaza | |
| 5,881,723 A | 3/1999 | Wallace et al. | |
| 5,884,622 A | 3/1999 | Younes | |
| 5,884,623 A | 3/1999 | Winter | |
| 5,891,023 A | 4/1999 | Lynn | |
| 5,901,704 A | 5/1999 | Estes et al. | |
| 5,904,141 A | 5/1999 | Estes et al. | |
| 5,909,731 A | 6/1999 | O'Mahony et al. | |
| 5,915,379 A | 6/1999 | Wallace et al. | |
| 5,915,380 A | 6/1999 | Wallace et al. | |
| 5,915,382 A | 6/1999 | Power | |
| 5,918,597 A | 7/1999 | Jones et al. | |
| 5,921,238 A | 7/1999 | Bourdon | |
| 5,921,920 A | 7/1999 | Marshall et al. | |
| 5,927,274 A | 7/1999 | Servidio et al. | |
| 5,934,274 A | 8/1999 | Merrick et al. | |
| 5,970,975 A | 10/1999 | Estes et al. | |
| 6,024,089 A | 2/2000 | Wallace et al. | |
| 6,029,664 A | 2/2000 | Zdrojkowski et al. | |
| 6,041,780 A | 3/2000 | Richard et al. | |
| 6,047,860 A | 4/2000 | Sanders | |
| 6,055,981 A | 5/2000 | Laswick et al. | |
| 6,059,732 A * | 5/2000 | Orr et al. ............. | 600/532 |
| 6,076,523 A | 6/2000 | Jones et al. | |
| 6,099,481 A | 8/2000 | Daniels et al. | |
| 6,105,575 A | 8/2000 | Estes et al. | |
| 6,116,240 A | 9/2000 | Merrick et al. | |
| 6,116,464 A | 9/2000 | Sanders | |

(56) References Cited

U.S. PATENT DOCUMENTS

| | | |
|---|---|---|
| 6,123,073 A | 9/2000 | Schlawin et al. |
| 6,123,074 A | 9/2000 | Hete et al. |
| 6,135,106 A | 10/2000 | Dirks et al. |
| 6,142,150 A | 11/2000 | O'Mahoney |
| 6,148,814 A | 11/2000 | Clemmer et al. |
| 6,152,129 A | 11/2000 | Berthon-Jones |
| 6,158,432 A | 12/2000 | Biondi et al. |
| 6,161,539 A | 12/2000 | Winter |
| 6,220,245 B1 | 4/2001 | Takabayashi et al. |
| 6,223,064 B1 | 4/2001 | Lynn et al. |
| 6,253,765 B1 | 7/2001 | Hğnelid et al. |
| 6,257,234 B1 | 7/2001 | Sun |
| 6,269,812 B1 | 8/2001 | Wallace et al. |
| 6,273,444 B1 | 8/2001 | Power |
| 6,279,569 B1 | 8/2001 | Berthon-Jones |
| 6,283,119 B1 | 9/2001 | Bourdon |
| 6,286,508 B1 | 9/2001 | Remmers et al. |
| 6,305,372 B1 | 10/2001 | Servidio |
| 6,305,373 B1 | 10/2001 | Wallace et al. |
| 6,305,374 B1 | 10/2001 | Zdrojkowski et al. |
| 6,321,748 B1 | 11/2001 | O'Mahoney |
| 6,325,785 B1 | 12/2001 | Babkes et al. |
| 6,342,039 B1 | 1/2002 | Lynn et al. |
| 6,357,438 B1 | 3/2002 | Hansen |
| 6,360,741 B2 | 3/2002 | Truschel |
| 6,360,745 B1 | 3/2002 | Wallace et al. |
| 6,369,838 B1 | 4/2002 | Wallace et al. |
| 6,371,114 B1 | 4/2002 | Schmidt et al. |
| 6,390,091 B1 | 5/2002 | Banner et al. |
| 6,412,483 B1 | 7/2002 | Jones et al. |
| 6,425,395 B1 | 7/2002 | Brewer et al. |
| 6,427,689 B1 | 8/2002 | Estes et al. |
| 6,439,229 B1 | 8/2002 | Du et al. |
| 6,467,478 B1 | 10/2002 | Merrick et al. |
| 6,484,719 B1 | 11/2002 | Berthon-Jones |
| 6,512,938 B2 | 1/2003 | Claure et al. |
| 6,532,957 B2 * | 3/2003 | Berthon-Jones ......... 128/204.21 |
| 6,532,958 B1 | 3/2003 | Buan et al. |
| 6,532,959 B1 | 3/2003 | Berthon-Jones |
| 6,532,960 B1 | 3/2003 | Yurko |
| 6,536,429 B1 | 3/2003 | Pavlov et al. |
| 6,536,432 B2 | 3/2003 | Truschel |
| 6,539,940 B2 | 4/2003 | Zdrojkowski et al. |
| 6,543,449 B1 | 4/2003 | Woodring et al. |
| 6,546,930 B1 | 4/2003 | Emerson et al. |
| 6,550,478 B2 | 4/2003 | Remmers et al. |
| 6,553,991 B1 | 4/2003 | Isaza |
| 6,553,992 B1 | 4/2003 | Berthon-Jones et al. |
| 6,557,553 B1 | 5/2003 | Borrello |
| 6,561,187 B2 | 5/2003 | Schmidt et al. |
| 6,571,795 B2 | 6/2003 | Bourdon |
| 6,575,163 B1 | 6/2003 | Berthon-Jones |
| 6,578,575 B1 | 6/2003 | Jonson |
| 6,609,016 B1 | 8/2003 | Lynn |
| 6,609,517 B1 | 8/2003 | Estes et al. |
| 6,615,834 B2 | 9/2003 | Gradon et al. |
| 6,622,726 B1 | 9/2003 | Du |
| 6,626,175 B2 | 9/2003 | Jafari et al. |
| 6,629,527 B1 | 10/2003 | Estes et al. |
| 6,640,806 B2 | 11/2003 | Yurko |
| 6,644,310 B1 | 11/2003 | Delache et al. |
| 6,644,312 B2 | 11/2003 | Berthon-Jones et al. |
| 6,644,316 B2 | 11/2003 | Bowman et al. |
| 6,659,101 B2 | 12/2003 | Berthon-Jones |
| 6,668,824 B1 | 12/2003 | Isaza et al. |
| 6,671,529 B2 | 12/2003 | Claure et al. |
| 6,675,801 B2 | 1/2004 | Wallace et al. |
| 6,688,307 B2 | 2/2004 | Berthon-Jones |
| 6,701,926 B2 | 3/2004 | Olsen et al. |
| 6,718,974 B1 | 4/2004 | Moberg |
| 6,722,365 B2 | 4/2004 | Nilsson et al. |
| 6,723,055 B2 | 4/2004 | Hoffman |
| 6,723,132 B2 | 4/2004 | Salehpoor |
| 6,725,447 B1 | 4/2004 | Gilman et al. |
| 6,739,337 B2 | 5/2004 | Isaza |
| 6,748,252 B2 | 6/2004 | Lynn et al. |
| 6,752,150 B1 | 6/2004 | Remmers et al. |
| 6,752,151 B2 | 6/2004 | Hill |
| 6,755,193 B2 | 6/2004 | Berthon-Jones et al. |
| 6,758,216 B1 | 7/2004 | Berthon-Jones et al. |
| 6,760,608 B2 | 7/2004 | Lynn |
| 6,761,165 B2 | 7/2004 | Strickland, Jr. |
| 6,761,167 B1 | 7/2004 | Nadjafizadeh et al. |
| 6,761,168 B1 | 7/2004 | Nadjafizadeh et al. |
| 6,789,541 B2 | 9/2004 | Olsen et al. |
| 6,796,305 B1 | 9/2004 | Banner et al. |
| 6,810,876 B2 | 11/2004 | Berthon-Jones |
| 6,814,074 B1 | 11/2004 | Nadjafizadeh et al. |
| 6,820,613 B2 | 11/2004 | Wenkebach et al. |
| 6,820,618 B2 | 11/2004 | Banner et al. |
| 6,823,866 B2 | 11/2004 | Jafari et al. |
| 6,837,242 B2 | 1/2005 | Younes |
| 6,843,250 B2 | 1/2005 | Efrati |
| 6,866,040 B1 | 3/2005 | Bourdon |
| 6,868,346 B2 | 3/2005 | Larson et al. |
| 6,874,503 B2 | 4/2005 | Rydgren |
| 6,910,480 B1 | 6/2005 | Berthon-Jones |
| 6,910,481 B2 | 6/2005 | Kimmel et al. |
| 6,920,875 B1 | 7/2005 | Hill et al. |
| 6,920,877 B2 | 7/2005 | Remmers et al. |
| 6,932,084 B2 | 8/2005 | Estes et al. |
| 6,945,248 B2 | 9/2005 | Berthon-Jones |
| 6,948,497 B2 | 9/2005 | Zdrojkowski et al. |
| 6,960,854 B2 | 11/2005 | Nadjafizadeh et al. |
| 6,962,155 B1 | 11/2005 | Sinderby |
| 6,986,347 B2 | 1/2006 | Hickle |
| 7,000,612 B2 | 2/2006 | Jafari et al. |
| 7,008,380 B1 | 3/2006 | Rees et al. |
| 7,013,892 B2 | 3/2006 | Estes et al. |
| 7,017,576 B2 | 3/2006 | Olsen et al. |
| 7,036,504 B2 | 5/2006 | Wallace et al. |
| 7,040,320 B2 | 5/2006 | Fjeld et al. |
| 7,044,129 B1 * | 5/2006 | Truschel et al. ......... 128/204.23 |
| 7,055,522 B2 | 6/2006 | Berthon-Jones |
| 7,066,173 B2 | 6/2006 | Banner et al. |
| 7,073,501 B2 | 7/2006 | Remmers et al. |
| 7,077,131 B2 | 7/2006 | Hansen |
| 7,081,095 B2 | 7/2006 | Lynn et al. |
| RE39,225 E | 8/2006 | Isaza et al. |
| 7,089,936 B2 | 8/2006 | Madaus et al. |
| 7,092,757 B2 | 8/2006 | Larson et al. |
| 7,100,607 B2 | 9/2006 | Zdrojkowski et al. |
| 7,100,608 B2 | 9/2006 | Brewer et al. |
| 7,100,609 B2 | 9/2006 | Berthon-Jones et al. |
| 7,107,991 B2 | 9/2006 | Kolobow |
| 7,117,438 B2 | 10/2006 | Wallace et al. |
| 7,137,389 B2 | 11/2006 | Berthon-Jones |
| 7,152,598 B2 | 12/2006 | Morris et al. |
| 7,168,429 B2 | 1/2007 | Matthews et al. |
| 7,195,028 B2 | 3/2007 | Basset et al. |
| 7,210,478 B2 | 5/2007 | Banner et al. |
| 7,229,430 B2 | 6/2007 | Hickle et al. |
| 7,267,122 B2 | 9/2007 | Hill |
| 7,270,126 B2 | 9/2007 | Wallace et al. |
| 7,275,540 B2 | 10/2007 | Bolam et al. |
| 7,296,573 B2 | 11/2007 | Estes et al. |
| 7,297,119 B2 | 11/2007 | Westbrook et al. |
| 7,331,343 B2 | 2/2008 | Schmidt et al. |
| 7,353,824 B1 | 4/2008 | Forsyth et al. |
| 7,367,337 B2 | 5/2008 | Berthon-Jones et al. |
| 7,369,757 B2 | 5/2008 | Farbarik |
| 7,370,650 B2 | 5/2008 | Nadjafizadeh et al. |
| 7,398,115 B2 | 7/2008 | Lynn |
| 7,406,870 B2 | 8/2008 | Seto |
| 7,428,902 B2 | 9/2008 | Du et al. |
| 7,448,381 B2 | 11/2008 | Sasaki et al. |
| 7,455,583 B2 | 11/2008 | Taya et al. |
| 7,460,959 B2 | 12/2008 | Jafari |
| 7,475,685 B2 | 1/2009 | Dietz et al. |
| 7,487,773 B2 | 2/2009 | Li |
| 7,509,957 B2 | 3/2009 | Duquette et al. |
| 7,527,056 B2 | 5/2009 | Turiello |
| 7,533,671 B2 | 5/2009 | Gonzalez et al. |
| 7,621,269 B2 | 11/2009 | Turiello |

(56) References Cited

U.S. PATENT DOCUMENTS

| | | |
|---|---|---|
| 7,644,713 B2 | 1/2010 | Berthon-Jones |
| 7,654,802 B2 | 2/2010 | Crawford, Jr. et al. |
| 7,661,428 B2 | 2/2010 | Berthon-Jones |
| 7,673,629 B2 | 3/2010 | Turiello |
| 7,677,247 B2 | 3/2010 | Turiello |
| 7,694,677 B2 | 4/2010 | Tang |
| 7,694,678 B2 | 4/2010 | Turiello |
| 7,717,112 B2 | 5/2010 | Sun et al. |
| 7,717,113 B2 | 5/2010 | Andrieux |
| D618,356 S | 6/2010 | Ross |
| 7,770,578 B2 | 8/2010 | Estes et al. |
| 7,784,461 B2 | 8/2010 | Figueiredo et al. |
| 7,810,496 B2 | 10/2010 | Estes et al. |
| 7,810,497 B2 | 10/2010 | Pittman et al. |
| 7,814,906 B2 | 10/2010 | Moretti |
| 7,823,588 B2 | 11/2010 | Hansen |
| 7,827,988 B2 | 11/2010 | Matthews et al. |
| 7,855,716 B2 | 12/2010 | McCreary et al. |
| 7,856,979 B2 | 12/2010 | Doshi et al. |
| D632,796 S | 2/2011 | Ross et al. |
| D632,797 S | 2/2011 | Ross et al. |
| 7,882,835 B2 | 2/2011 | Eger et al. |
| 7,886,739 B2 | 2/2011 | Soliman et al. |
| 7,886,740 B2 | 2/2011 | Thomas et al. |
| 7,891,354 B2 | 2/2011 | Farbarik |
| 7,893,560 B2 | 2/2011 | Carter |
| 7,905,231 B2 | 3/2011 | Chalvignac |
| 7,918,222 B2 | 4/2011 | Chen |
| 7,918,223 B2 | 4/2011 | Soliman et al. |
| 7,920,067 B2 | 4/2011 | Durtschi et al. |
| 7,928,852 B2 | 4/2011 | Durtschi et al. |
| D638,852 S | 5/2011 | Skidmore et al. |
| 7,934,499 B2 | 5/2011 | Berthon-Jones |
| 7,938,114 B2 | 5/2011 | Matthews et al. |
| 7,963,283 B2 | 6/2011 | Sinderby |
| 7,984,712 B2 | 7/2011 | Soliman et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| 8,002,154 B2 | 8/2011 | Fontela et al. |
| D645,158 S | 9/2011 | Sanchez et al. |
| 8,021,309 B2 | 9/2011 | Zilberg |
| 8,021,310 B2 | 9/2011 | Sanborn et al. |
| 8,033,280 B2 | 10/2011 | Heinonen |
| D649,157 S | 11/2011 | Skidmore et al. |
| 8,051,853 B2 | 11/2011 | Berthon-Jones |
| 8,070,709 B2 | 12/2011 | Childers |
| 8,083,677 B2 | 12/2011 | Rohde |
| D652,521 S | 1/2012 | Ross et al. |
| D652,936 S | 1/2012 | Ross et al. |
| 8,105,310 B2 | 1/2012 | Klein |
| D653,749 S | 2/2012 | Winter et al. |
| 8,113,062 B2 | 2/2012 | Graboi et al. |
| 8,122,885 B2 | 2/2012 | Berthon-Jones et al. |
| D655,405 S | 3/2012 | Winter et al. |
| D655,809 S | 3/2012 | Winter et al. |
| D656,237 S | 3/2012 | Sanchez et al. |
| 8,136,521 B2 | 3/2012 | Matthews et al. |
| 8,152,116 B2 | 4/2012 | Westberg |
| RE43,398 E | 5/2012 | Honkonen et al. |
| 8,181,643 B2 | 5/2012 | Friedberg |
| 8,181,648 B2 | 5/2012 | Perine et al. |
| 8,181,649 B2 | 5/2012 | Brunner |
| 8,187,184 B2 | 5/2012 | Muller et al. |
| 8,210,173 B2 | 7/2012 | Vandine |
| 8,210,174 B2 | 7/2012 | Farbarik |
| 8,211,128 B1 | 7/2012 | Facundus et al. |
| 8,216,159 B1 | 7/2012 | Leiboff |
| 8,217,218 B2 | 7/2012 | Court et al. |
| 8,225,796 B2 | 7/2012 | Davenport et al. |
| 8,235,930 B1 | 8/2012 | McCall |
| 8,240,684 B2 | 8/2012 | Ross et al. |
| 8,251,923 B2 | 8/2012 | Carrez et al. |
| 8,256,418 B2 | 9/2012 | Bassin |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,288,607 B2 | 10/2012 | Court et al. |
| 8,302,600 B2 | 11/2012 | Andrieux et al. |
| 8,302,602 B2 | 11/2012 | Andrieux et al. |
| 2002/0014240 A1 | 2/2002 | Truschel |
| 2002/0053345 A1* | 5/2002 | Jafari et al. .............. 128/204.23 |
| 2002/0185126 A1 | 12/2002 | Krebs |
| 2003/0010339 A1 | 1/2003 | Banner et al. |
| 2003/0158466 A1 | 8/2003 | Lynn et al. |
| 2003/0159695 A1 | 8/2003 | Younes |
| 2003/0221689 A1 | 12/2003 | Berthon-Jones |
| 2004/0050387 A1 | 3/2004 | Younes |
| 2004/0074492 A1 | 4/2004 | Berthon-Jones |
| 2004/0089561 A1 | 5/2004 | Herman |
| 2004/0163648 A1 | 8/2004 | Burton |
| 2004/0187870 A1 | 9/2004 | Matthews et al. |
| 2005/0039748 A1 | 2/2005 | Andrieux |
| 2005/0109340 A1 | 5/2005 | Tehrani |
| 2005/0139212 A1 | 6/2005 | Bourdon |
| 2005/0172965 A1 | 8/2005 | Thulin |
| 2005/0188991 A1 | 9/2005 | Sun et al. |
| 2005/0241639 A1 | 11/2005 | Zilberg |
| 2006/0000475 A1 | 1/2006 | Matthews et al. |
| 2006/0011200 A1 | 1/2006 | Remmers et al. |
| 2006/0086357 A1 | 4/2006 | Soliman et al. |
| 2006/0102180 A1 | 5/2006 | Berthon-Jones |
| 2006/0112959 A1 | 6/2006 | Mechlenburg et al. |
| 2006/0118112 A1 | 6/2006 | Cattano et al. |
| 2006/0144144 A1 | 7/2006 | Seto |
| 2006/0150974 A1 | 7/2006 | Berthon-Jones |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0174883 A1 | 8/2006 | Aylsworth et al. |
| 2006/0189880 A1 | 8/2006 | Lynn et al. |
| 2006/0195041 A1 | 8/2006 | Lynn et al. |
| 2006/0201505 A1 | 9/2006 | Remmers et al. |
| 2006/0217633 A1 | 9/2006 | Glocker et al. |
| 2006/0235324 A1 | 10/2006 | Lynn |
| 2006/0241708 A1 | 10/2006 | Boute |
| 2006/0247508 A1 | 11/2006 | Fennell |
| 2006/0249150 A1 | 11/2006 | Dietz et al. |
| 2006/0249156 A1 | 11/2006 | Moretti |
| 2006/0254588 A1 | 11/2006 | Brewer et al. |
| 2006/0264762 A1 | 11/2006 | Starr |
| 2006/0272642 A1 | 12/2006 | Chalvignac |
| 2006/0278218 A1 | 12/2006 | Hoffman |
| 2007/0000494 A1 | 1/2007 | Banner et al. |
| 2007/0017515 A1 | 1/2007 | Wallace et al. |
| 2007/0027375 A1 | 2/2007 | Melker et al. |
| 2007/0028921 A1 | 2/2007 | Banner et al. |
| 2007/0044796 A1* | 3/2007 | Zdrojkowski et al. .. 128/204.18 |
| 2007/0068530 A1 | 3/2007 | Pacey |
| 2007/0072541 A1 | 3/2007 | Daniels, II et al. |
| 2007/0077200 A1 | 4/2007 | Baker |
| 2007/0089738 A1 | 4/2007 | Soliman et al. |
| 2007/0093721 A1 | 4/2007 | Lynn et al. |
| 2007/0101992 A1 | 5/2007 | Soliman et al. |
| 2007/0129647 A1 | 6/2007 | Lynn |
| 2007/0135736 A1 | 6/2007 | Addington |
| 2007/0144522 A1 | 6/2007 | Eger et al. |
| 2007/0149860 A1 | 6/2007 | Lynn et al. |
| 2007/0157931 A1 | 7/2007 | Parker et al. |
| 2007/0163579 A1 | 7/2007 | Li et al. |
| 2007/0191688 A1 | 8/2007 | Lynn |
| 2007/0191697 A1 | 8/2007 | Lynn et al. |
| 2007/0215154 A1 | 9/2007 | Borrello |
| 2007/0221224 A1 | 9/2007 | Pittman et al. |
| 2007/0227537 A1 | 10/2007 | Bemister et al. |
| 2007/0251532 A1 | 11/2007 | Friedberg |
| 2007/0272241 A1 | 11/2007 | Sanborn et al. |
| 2007/0277823 A1 | 12/2007 | Al-Ali et al. |
| 2007/0283958 A1 | 12/2007 | Naghavi |
| 2007/0284361 A1 | 12/2007 | Nadjafizadeh et al. |
| 2008/0000478 A1 | 1/2008 | Matthiessen et al. |
| 2008/0000479 A1 | 1/2008 | Elaz et al. |
| 2008/0041382 A1 | 2/2008 | Matthews et al. |

(56) References Cited

U.S. PATENT DOCUMENTS

| | | |
|---|---|---|
| 2008/0041383 A1 | 2/2008 | Matthews et al. |
| 2008/0051674 A1 | 2/2008 | Davenport et al. |
| 2008/0053441 A1 | 3/2008 | Gottlib et al. |
| 2008/0053442 A1 | 3/2008 | Estes et al. |
| 2008/0053443 A1 | 3/2008 | Estes et al. |
| 2008/0053444 A1 | 3/2008 | Estes et al. |
| 2008/0066752 A1 | 3/2008 | Baker et al. |
| 2008/0066753 A1 | 3/2008 | Martin et al. |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0081974 A1 | 4/2008 | Pav |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0168988 A1 | 7/2008 | Lu |
| 2008/0178880 A1 | 7/2008 | Christopher et al. |
| 2008/0178882 A1 | 7/2008 | Christopher et al. |
| 2008/0185002 A1 | 8/2008 | Berthon-Jones et al. |
| 2008/0200775 A1 | 8/2008 | Lynn |
| 2008/0200819 A1 | 8/2008 | Lynn et al. |
| 2008/0221469 A1 | 9/2008 | Shevchuk |
| 2008/0251079 A1 | 10/2008 | Richey |
| 2008/0295837 A1 | 12/2008 | McCormick et al. |
| 2008/0302359 A1 | 12/2008 | Loomas et al. |
| 2009/0014007 A1 | 1/2009 | Brambilla et al. |
| 2009/0050153 A1 | 2/2009 | Brunner |
| 2009/0082653 A1 | 3/2009 | Rohde |
| 2009/0088613 A1 | 4/2009 | Marttila et al. |
| 2009/0093697 A1 | 4/2009 | Mir et al. |
| 2009/0137927 A1 | 5/2009 | Miller |
| 2009/0149730 A1 | 6/2009 | McCrary |
| 2009/0165795 A1 | 7/2009 | Nadjafizadeh et al. |
| 2009/0171176 A1 | 7/2009 | Andersohn |
| 2009/0171226 A1 | 7/2009 | Campbell et al. |
| 2009/0178675 A1 | 7/2009 | Turiello |
| 2009/0178676 A1 | 7/2009 | Villax et al. |
| 2009/0194100 A1 | 8/2009 | Minagi |
| 2009/0205661 A1 | 8/2009 | Stephenson et al. |
| 2009/0205663 A1 | 8/2009 | Vandine et al. |
| 2009/0229605 A1 | 9/2009 | Efrati et al. |
| 2009/0241951 A1 | 10/2009 | Jafari et al. |
| 2009/0241952 A1 | 10/2009 | Nicolazzi et al. |
| 2009/0241953 A1 | 10/2009 | Vandine et al. |
| 2009/0241955 A1 | 10/2009 | Jafari et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247891 A1 | 10/2009 | Wood |
| 2009/0250061 A1 | 10/2009 | Marasigan |
| 2009/0272382 A1 | 11/2009 | Euliano et al. |
| 2009/0281481 A1 | 11/2009 | Harding |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2009/0308398 A1 | 12/2009 | Ferdinand et al. |
| 2009/0314294 A1 | 12/2009 | Chalvignac |
| 2009/0318851 A1 | 12/2009 | Schenck |
| 2010/0011307 A1 | 1/2010 | Desfossez et al. |
| 2010/0018529 A1 | 1/2010 | Chalvignac |
| 2010/0024819 A1 | 2/2010 | Tiedje |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0065057 A1 | 3/2010 | Berthon-Jones |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078018 A1 | 4/2010 | Heinonen |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0081958 A1 | 4/2010 | She |
| 2010/0101574 A1 | 4/2010 | Bassin |
| 2010/0101576 A1 | 4/2010 | Berthon-Jones |
| 2010/0116276 A1 | 5/2010 | Bayasi |
| 2010/0137737 A1 | 6/2010 | Addington et al. |
| 2010/0139660 A1 | 6/2010 | Adahan |
| 2010/0147303 A1 | 6/2010 | Jafari et al. |
| 2010/0186741 A1 | 7/2010 | Aylsworth et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0234758 A1 | 9/2010 | de Menezes |
| 2010/0236553 A1 | 9/2010 | Jafari et al. |
| 2010/0236555 A1 | 9/2010 | Jafari et al. |
| 2010/0242961 A1 | 9/2010 | Mougel et al. |
| 2010/0252048 A1 | 10/2010 | Young et al. |
| 2010/0258123 A1 | 10/2010 | Somaiya et al. |
| 2010/0262038 A1 | 10/2010 | Tan et al. |
| 2010/0282259 A1 | 11/2010 | Figueiredo et al. |
| 2010/0288283 A1 | 11/2010 | Campbell et al. |
| 2010/0300446 A1 | 12/2010 | Nicolazzi et al. |
| 2010/0331768 A1 | 12/2010 | Hedmann et al. |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0034863 A1 | 2/2011 | Hoffa |
| 2011/0041849 A1 | 2/2011 | Chen et al. |
| 2011/0041850 A1 | 2/2011 | Vandine et al. |
| 2011/0061648 A1 | 3/2011 | Durtschi et al. |
| 2011/0071367 A1 | 3/2011 | Court et al. |
| 2011/0077549 A1 | 3/2011 | Kitai et al. |
| 2011/0100373 A1 | 5/2011 | Efrati et al. |
| 2011/0125052 A1 | 5/2011 | Davenport et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132363 A1 | 6/2011 | Chalvignac |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0178427 A1 | 7/2011 | Tan et al. |
| 2011/0196251 A1 | 8/2011 | Jourdain et al. |
| 2011/0201956 A1 | 8/2011 | Alferness et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0220112 A1 | 9/2011 | Connor |
| 2011/0226250 A1 | 9/2011 | LaBollita et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |

(56) References Cited

U.S. PATENT DOCUMENTS

| | | |
|---|---|---|
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2011/0284003 A1 | 11/2011 | Douglas et al. |
| 2011/0290246 A1 | 12/2011 | Zachar |
| 2011/0293706 A1 | 12/2011 | Ludwig et al. |
| 2011/0313689 A1 | 12/2011 | Holley et al. |
| 2012/0000466 A1 | 1/2012 | Rapoport |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0006328 A1 | 1/2012 | Berthon-Jones |
| 2012/0022441 A1 | 1/2012 | Kelly et al. |
| 2012/0029317 A1 | 2/2012 | Doyle et al. |
| 2012/0030611 A1 | 2/2012 | Skidmore |
| 2012/0060835 A1 | 3/2012 | Mashak |
| 2012/0060841 A1 | 3/2012 | Crawford, Jr. et al. |
| 2012/0065533 A1 | 3/2012 | Carrillo, Jr. et al. |
| 2012/0071729 A1 | 3/2012 | Doyle et al. |
| 2012/0083729 A1 | 4/2012 | Childers |
| 2012/0090610 A1 | 4/2012 | O'Connor et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0139734 A1 | 6/2012 | Olde et al. |
| 2012/0150057 A1 | 6/2012 | Mantri |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0215081 A1 | 8/2012 | Euliano et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0304995 A1 | 12/2012 | Kauc |
| 2012/0304997 A1 | 12/2012 | Jafari et al. |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0186400 A1 | 7/2013 | Jafari et al. |
| 2013/0186401 A1 | 7/2013 | Jafari et al. |

FOREIGN PATENT DOCUMENTS

| | | |
|---|---|---|
| EP | 1270036 | 1/2003 |
| WO | WO 94/23780 A | 10/1994 |
| WO | WO 98/06449 A | 2/1998 |
| WO | WO 00/10634 A | 3/2000 |
| WO | WO 00/45880 A | 8/2000 |
| WO | WO 01/74430 A | 10/2001 |
| WO | WO 02/28460 A | 4/2002 |
| WO | WO 03/055552 A1 | 7/2003 |
| WO | WO 04000114 | 12/2003 |
| WO | WO 2004/084980 A | 10/2004 |
| WO | WO 2005/105189 | 11/2005 |
| WO | WO 2006/137784 A1 | 12/2006 |
| WO | WO 07145948 | 12/2007 |
| WO | WO 2009123981 | 10/2009 |

OTHER PUBLICATIONS

U.S. Appl. No. 12/238,248, Office Action dated Oct. 15, 2012, 12 pgs.
U.S. Appl. No. 12/238,248, Office Action dated May 14, 2012, 12 pgs.
U.S. Appl. No. 12/242,756, Supplemental Notice of Allowability dated Aug. 27, 2012, 2 pgs.
U.S. Appl. No. 12/242,741, Supplemental Notice of Allowability dated Aug. 27, 2012, 2 pgs.
U.S. Appl. No. 12/408,414, Amendment and Response filed Sep. 5, 2012, 7 pgs.
U.S. Appl. No. 12/414,419, Amendment and Response filed Aug. 27, 2012, 8 pgs.
U.S. Appl. No. 12/395,332, Notice of Allowance dated Dec. 24, 2012, 8 pgs.
U.S. Appl. No. 12/408,414, Notice of Allowance dated Dec. 10, 2012, 10 pgs.
U.S. Appl. No. 12/414,419, Notice of Allowance dated Jan. 8, 2013, 7 pgs.
U.S. Appl. No. 12/238,248, Advisory Action dated Jan. 4, 2013, 3 pgs.
PCT International Search Report and Written Opinion in Application PCT/US2010/025485, dated Feb. 27, 2009, 8 pgs.
PCT International Search Report and Written Opinion in Application PCT/2009/038810, dated Jul. 6, 2009, 16 pgs.
PCT International Search Report and Written Opinion in Application PCT/2009/038815, dated Jul. 1, 2009, 14 pgs.
PCT International Search Report and Written Opinion in Application PCT/US09/038811, dated Jun. 7, 2009, 13 pgs.
PCT International Search Report and Written Opinion in Application PCT/US2009/038819, dated Jun. 26, 2009, 12 pgs.
PCT International Search Report and Written Opinion in Application PCT/US2009/038820, dated Jul. 22, 2009, 14 pgs.
PCT International Search Report and Written Opinion in Application PCT/US2009038818, dated Jul. 14, 2009, 15 pgs.
PCT International Search Report and Written Opinion in Application PCT/US201/0026618, dated Jun. 22, 2010, 19 pgs.
U.S. Appl. No. 12/242,741, Office Action dated Jan. 10, 2012, 7 pgs.
U.S. Appl. No. 12/242,756, Office Action dated Jan. 10, 2012, 7 pgs.
U.S. Appl. No. 12/334,354, Notice of Allowance dated Jan. 27, 2012, 7 pgs.
U.S. Appl. No. 12/414,419, Office Action dated Jan. 20, 2012, 15 pgs.
Younes, M, et al., "Control of breathing relevant to mechanical ventilation", in Physiological Basis of Ventilatory Support, J.J. Marini and A.S. Slutsky, Ed., New York, Marcel Dekker, 1998, pp. 1-73.
Crooke, P.S. et al., "Patient-ventilator interaction: A general model for nonpassive mechanical ventilation", 1998, AMA Journal of Mathematics Applied in Medicine and Biology, 15, pp. 321-337.
U.S. Appl. No. 12/238,248, Office Action dated Apr. 26, 2013, 13 pgs.
U.S. Appl. No. 12/242,741, Notice of Allowance dated Jun. 5, 2012, 5 pgs.
U.S. Appl. No. 12/242,756, Notice of Allowance dated Jun. 5, 2012, 5 pgs.
U.S. Appl. No. 12/408,408, Notice of Allowance dated Jun. 4, 2012, 10 pgs.
U.S. Appl. No. 12/408,414, Office Action dated Jun. 20, 2012, 9 pgs.
U.S. Appl. No. 12/414,419, Office Action dated Jul. 18, 2012, 16 pgs.
U.S. Appl. No. 12/334,354, Notice of Allowance dated Oct. 5, 2012, 5 pgs.
U.S. Appl. No. 12/395,332, Office Action dated Sep. 13, 2012, 9 pgs.
U.S. Appl. No. 13/565,595, Notice of Allowance dated Nov. 2, 2012, 12 pgs.
U.S. Appl. No. 12/414,419, Notice of Allowance dated Sep. 19, 2012, 8 pgs.
U.S. Appl. No. 13/565,595, Notice of Allowance dated Feb. 25, 2013, 8 pgs.

* cited by examiner

SYSTEM AND METHOD FOR DETERMINING VENTILATOR LEAKAGE DURING STABLE PERIODS WITHIN A BREATH

This application is a National Stage Application of PCT/US2009/038819, filed 30 Mar. 2009, which claims benefit of U.S. Ser. No. 61/041,070, filed 31 Mar. 2008 and U.S. Ser. No. 61/122,288, filed 12 Dec. 2008 and which applications are incorporated herein by reference. To the extent appropriate, a claim of priority is made to each of the above disclosed applications.

BACKGROUND

The present description pertains to ventilator devices used to provide breathing assistance. Modern ventilator technologies commonly employ positive pressure to assist patient ventilation. For example, after determining a patient-initiated or timed trigger, the ventilator delivers a specified gas mixture into an inhalation airway connected to the patient to track a specified desired pressure or flow trajectory, causing or assisting the patient's lungs to fill. Upon reaching the end of the inspiration, the added support is removed and the patient is allowed to passively exhale and the ventilator controls the gas flow through the system to maintain a designated airway pressure level (PEEP) during the exhalation phase. Other types of ventilators are non-triggered, and mandate a specified breathing pattern regardless of patient effort.

Modern ventilators typically include microprocessors or other controllers that employ various control schemes. These control schemes are used to command a pneumatic system (e.g., valves) that regulates the flow rates of breathing gases to and from the patient. Closed-loop control is often employed, using data from pressure/flow sensors.

Many therapeutic settings involve the potential for leaks occurring at various locations on the ventilator device. The magnitude of these leaks can vary from setting to setting, and/or dynamically within a particular setting, dependent upon a host of variables. Leaks can impair triggering (transition into inhalation phase) and cycling (transition into exhalation phase) of the ventilator; and thus cause problems with patient-device synchrony; undesirably increase patient breathing work; degrade advisory information available to treatment providers; and/or otherwise comprise the desired respiratory therapy.

Determining Ventilator Leakage from Data Taken During a Stable Period within a Breath This disclosure describes systems and methods for compensating for leaks in a ventilation system based on data obtained during periods within a breath in which the patient is neither inhaling nor exhaling. The methods and systems described herein more accurately and quickly identify changes in leakage. This information is then to estimate leakage later in the same breath or in subsequent breaths to calculate a more accurate estimate of instantaneous leakage based on current conditions. The estimated leakage is then used to compensate for the leak flow rates, reduce the patient's work of breathing and increase the patient's comfort (patient-ventilator breath phase transition synchrony). Without the improvements provided by the disclosed methods and systems, changes in the leak conditions during a breath may not be identified and/or accurately characterized until the following breath or later.

In part, this disclosure describes a method for identifying leakage in a respiratory gas supply system. In the method, data indicative of at least one of pressure and flow in the respiratory gas supply system is monitored during the delivery of respiratory gas to a patient. The method includes identifying that the data meet at least one stability criterion indicating that pressure and flow conditions have been stable for a period of time within a breath. These stability criteria are selected to identify stable periods within a breath in which the patient is neither inhaling nor exhaling. Upon identification of a stable period, the method calculates leakage information based at least in part on the data taken during the period of time within the breath. This leakage information may take the form of one or more orifice constants, leak conductances, leak factors, exponents, or other leak characteristics as required by the leakage model utilized by the ventilator to estimate instantaneous leakage from the current status (e.g., pressure or flow) of the ventilator. The method then uses the leakage information to determine a leakage rate in subsequent calculations performed after the stable period. This may include estimating an instantaneous leakage after the period of time based at least in part on the leakage information derived from data taken during the stable period.

This disclosure also describes a respiratory gas supply system that identifies stable periods within a breath and derives leakage information for use later in the same breath or in subsequent breaths in estimating instantaneous leakage. The system includes a pressure generating system capable of controlling the flow of breathing gas through a patient circuit and a patient interface to a patient, a stable period identification module that identifies a stable period within a breath, and a leak compensation module that calculates leakage information using data obtained during the stable period identified by the stable period identification module and that calculates, during subsequent stable and unstable periods within the breath or a later breath, an instantaneous leakage rate based on the leakage information.

This disclosure also describes another method for determining leakage from a respiratory gas supply system providing respiratory gas to a breathing patient. The method includes identifying at least one stable period within a patient breath and calculating leakage information based on pressure and flow data obtained during the at least one stable period. The method also, at times subsequent to the stable period, estimates the leakage from the respiratory gas supply system based on the leakage information calculated from the data obtained during the at least one stable period and the current data.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of described technology and are

DETAILED DESCRIPTION

Although the techniques introduced above and discussed in detail below may be implemented for a variety of medical devices, the present disclosure will discuss the implementation of these techniques in the context of a medical ventilator for use in providing ventilation support to a human patient. The reader will understand that the technology described in the context of a medical ventilator for human patients could be adapted for use with other systems such as ventilators for non-human patients and general gas transport systems in which leaks may cause a degradation of performance.

As a threshold issue, the terms "leakage" and "leak" shall be used to refer to only the inadvertent escape of gas from unknown locations in ventilation system and does not include any measured or known intentional discharges of gas (such as through an exhaust port, relief valve or an expiratory limb). A leakage may be expressed as a rate (flow) or a volume depending on the situation.

Figure 1:
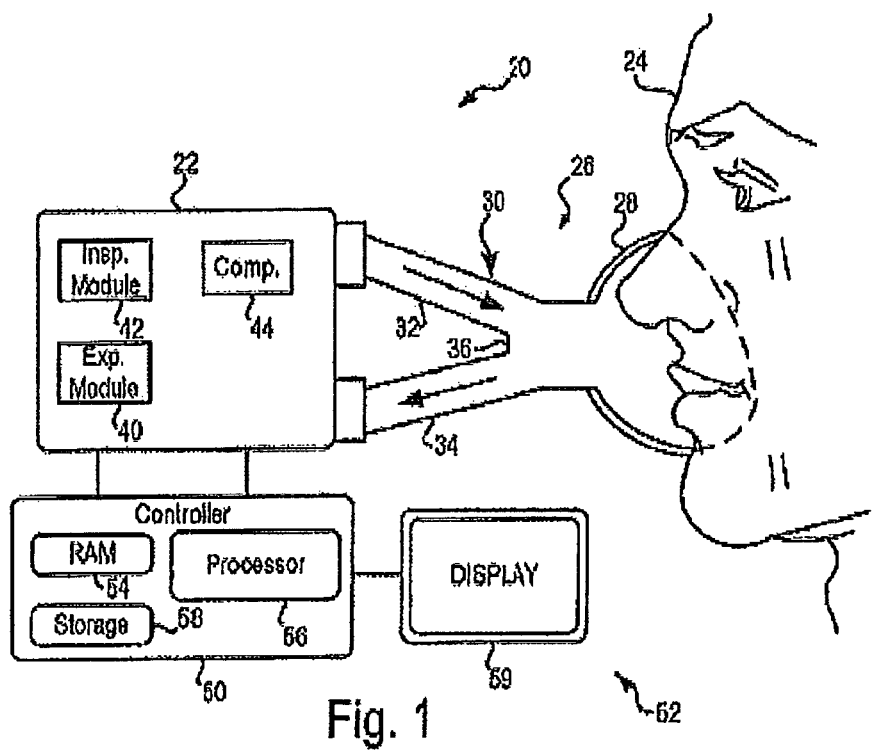
FIG. 1 illustrates an embodiment of a ventilator connected to a human patient.

FIG. 1 illustrates an embodiment of a respiratory gas supply system in the form of a ventilator 20 connected to a human patient 24. Ventilator 20 includes a pneumatic system 22 (also referred to as a pressure generating system 22) for circulating breathing gases to and from patient 24 via the ventilation tubing system 26, which couples the patient to the pneumatic system via physical patient interface 28 and ventilator circuit 30. Ventilator circuit 30 could be a dual-limb circuit (as shown) for carrying gas to and from the patient or a single-limb system that delivers breathing gas to the patient after which it is discharged directly to the atmosphere without being returned to the pneumatic system 22. In a dual-limb embodiment as shown, a wye fitting 36 may be provided as shown to couple the patient interface 28 to the inspiratory limb 32 and the expiratory limb 34 of the circuit 30. Exhaled gas is discharged from the expiratory limb 34 through the ventilator 20 which discharge of gas may be both monitored and controlled by the ventilator 20 as part of the delivery of gas to the patient.

The present systems and methods have proved particularly advantageous in noninvasive settings, such as with facial breathing masks, as those settings typically are more susceptible to leaks. However, leaks do occur in a variety of settings, and the present description contemplates that the patient interface may be invasive or non-invasive, and of any configuration suitable for communicating a flow of breathing gas from the patient circuit to an airway of the patient. Examples of suitable patient interface devices include a nasal mask, nasal/oral mask (which is shown in FIG. 1), nasal prong, full-face mask, tracheal tube, endotracheal tube, nasal pillow, etc.

Pneumatic system 22 may be configured in a variety of ways. In the present example, system 22 includes an expiratory module 40 coupled with an expiratory limb 34 and an inspiratory module 42 coupled with an inspiratory limb 32. Compressor 44 or another source(s) of pressurized gas (e.g., air and oxygen) is coupled with inspiratory module 42 to provide a gas source for ventilatory support via inspiratory limb 32.

The pneumatic system may include a variety of other components, including sources for pressurized air and/or oxygen, mixing modules, valves, sensors, tubing, accumulators, filters, etc. Controller 50 is operatively coupled with pneumatic system 22, signal measurement and acquisition systems, and an operator interface 52 may be provided to enable an operator to interact with the ventilator (e.g., change ventilator settings, select operational modes, view monitored parameters, etc.). Controller 50 may include memory 54, one or more processors 56, storage 58, and/or other components of the type commonly found in command and control computing devices.

The memory 54 is computer-readable storage media that stores software that is executed by the processor 56 and which controls the operation of the ventilator 20. In an embodiment, the memory 54 comprises one or more solid-state storage devices such as flash memory chips. hi an alternative embodiment, the memory 54 may be mass storage connected to the processor 56 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 56. Computer-readable storage media includes volatile and non-volatile, removable and non-removable media implemented in any method or technology for storage of information such as computer-readable instructions, data structures, program modules or other data. Computer-readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

As described in more detail below, controller 50 issues commands to pneumatic system 22 in order to control the breathing assistance provided to the patient by the ventilator. The specific commands may be based on inputs received from patient 24, pneumatic system 22 and sensors, operator interface 52 and/or other components of the ventilator. In the depicted example, operator interface includes a display 59 that is touch-sensitive, enabling the display to serve both as an input and output device.

Figure 2:
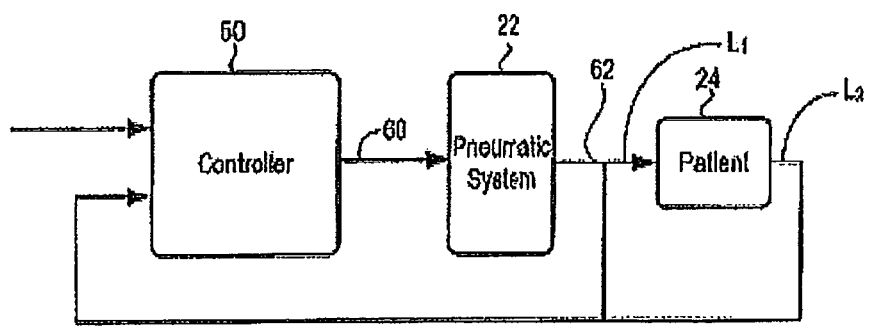
FIG. 2 schematically depicts exemplary systems and methods of ventilator control.

FIG. 2 schematically depicts exemplary systems and methods of ventilator control. As shown, controller 50 issues control commands 60 to drive pneumatic system 22 and thereby circulate breathing gas to and from patient 24. The depicted schematic interaction between pneumatic system 22 and patient 24 may be viewed in terms of pressure and/or flow "signals." For example, signal 62 may be an increased pressure which is applied to the patient via inspiratory limb 32. Control commands 60 are based upon inputs received at controller 50 which may include, among other things, inputs from operator interface 52, and feedback from pneumatic system 22 (e.g., from pressure/flow sensors) and/or sensed from patient 24.

In many cases, it may be desirable to establish a baseline pressure and/or flow trajectory for a given respiratory therapy session. The volume of breathing gas delivered to the patient's lung ($L_1$) and the volume of the gas exhaled by the patient ($L_2$) are measured or determined, and the measured or predicted/estimated leaks are accounted for to ensure accurate delivery and data reporting and monitoring. Accordingly, the more accurate the leak estimation, the better the baseline calculation of delivered and exhaled volume as well as event detection (triggering and cycling phase transitions).

When modeling the delivery of gas to and from a patient 24 via a closed-circuit ventilator, one simple assumption is that compliance of the ventilator circuit 30 is fixed and that all gas injected into the ventilator circuit 30 that does not exit the circuit 30 via the expiratory limb 34 fills the circuit as well as the patient's lungs and causes an increase in pressure. As gas is injected ($L_1$), the lung responds to the increased gas pressure in the circuit 30 by expanding. The amount the lung expands is proportional to the lung compliance and is defined as a function of gas pressure differential (Compliance=volume delivered/pressure difference).

Errors may be introduced due to leaks in the system. For example, in a perfect dual-limb system the difference in gas input into the system and gas exiting the system at any point in time is the instantaneous lung flow of the patient. However, if this method is used to calculate lung flow when there is, in actuality, some gas that is unknowingly leaking out the instantaneous lung flow calculation will be incorrect. Lung flow calculations may be used for many different purposes such as synchronizing the operation of the ventilatory support provided by the ventilator 20 with a patient's actual breathing. In order to improve the overall operation of the ventilator, then, it is desirable to, where possible, identify and account for any leaks in the system that may affect the lung flow calculation.

Leaks may occur at any point in the ventilation tubing system 26. The term ventilation tubing system 26 is used herein to describe the ventilator circuit 30, any equipment attached to or used in the ventilator circuit 30 such as water traps, monitors, drug delivery devices, etc. (not shown), and the patient interface 28. Depending on the embodiment, this may include some equipment contained in the inspiration module 42 and/or the expiration module 40. When referring to leaks in or from the ventilation tubing system 26, such leaks include leaks within the tubing system 26 and leaks where the tubing system 26 connects to the pressure generator 22 or the patient 24. Thus, leaks from the ventilation tubing system 26 include leaks from the ventilator circuit 30, leaks from the patient interface 28 (e.g., masks may be provided with holes or other pressure relief devices through which some leakage may occur), leaks from the points of connection between components in the tubing system 26 (e.g., due to a poor connection between the patient interface 28 and the circuit 30), and leaks from where the patient interface 28 connects to the patient 24 (e.g., leaks around the edges of a mask due to a poor fit or patient movement).

Figure 3:
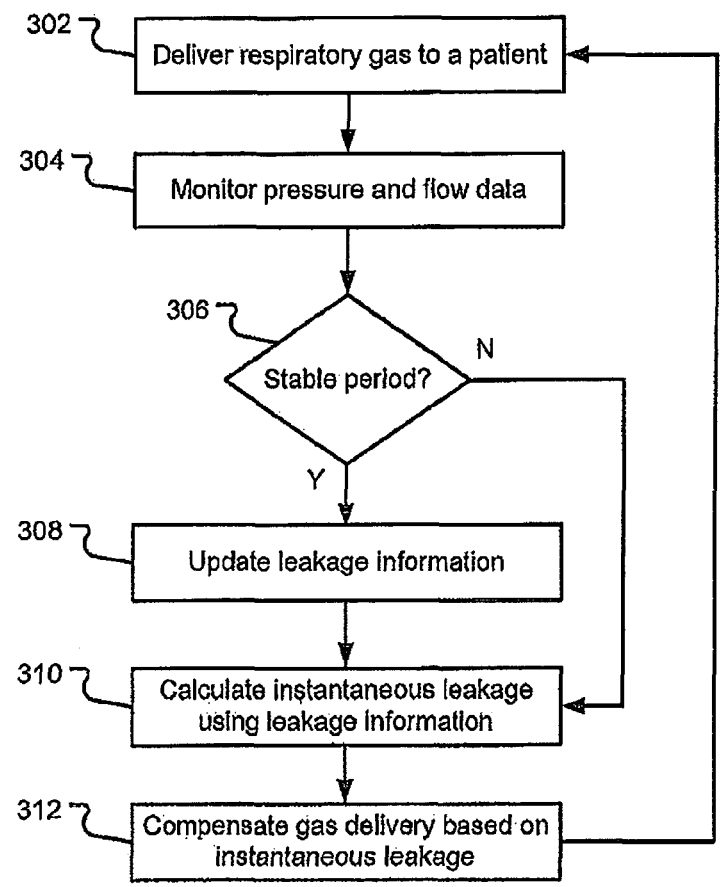
FIG. 3 illustrates an embodiment of a method for identifying the leakage from a ventilation tubing system of a respiratory gas supply system.

FIG. 3 illustrates an embodiment of a method for identifying the leakage from a ventilation tubing system of a respiratory gas supply system. In the embodiment shown, a ventilator such any of those described above is delivering gas to a patient as illustrated by the respiratory gas delivery operation 302. The patient may be initiating breaths on his/her own (i.e., actively breathing) or the delivery of gas may be completely controlled by the ventilator so that respiratory gas is forced into and out of the lungs of the patient without any action on the patient's part.

In addition to delivering gas, the method 300 includes a monitoring operation 304 in which data on the pressure, flow and other operational parameters are gathered while the ventilator is delivering gas. Monitoring refers to taking measurements or otherwise obtaining data indicative of the operational condition of the ventilator (e.g., pressure or flow) at one or more locations. For example, in a dual-limb ventilator embodiment the pressure and flow in both the inspiratory limb and the expiratory limb may be recorded by the monitoring operation 304. In an embodiment in which a sensor or sensors are provided at a wye or the patient interface, the monitoring operation 304 may include obtaining data from these sensors.

The monitoring operation 304 may include periodically or occasionally requesting or receiving data from a sensor or other data source. For example, in a digital system monitoring may be performed by gathering data from each sensor every time the sensor is polled by the ventilator's control system or every computational cycle in which a data analysis routine is performed. In one such embodiment, monitoring includes obtaining data from all sensors every computational cycle). Monitoring may also be performed continuously such as in an analog system in which analog signals from sensors are continuously feed into comparators or other analog components for evaluation.

As part of the monitoring operation 304, the data are evaluated in order to identify stable periods of operation in which the operational conditions such as pressure and flow within the ventilation tubing system are relatively constant and indicative of a period during which the patient is neither breathing in nor breathing out significantly. Such stable periods, for example, may appear at the end of an inhalation just prior to the patient beginning exhalation, at the end of an exhalation prior to the patient initiating the next inhalation and at times when a patient is, consciously or unconsciously, holding his/her breath.

In an embodiment, stable periods are identified by comparing the data obtained by the monitoring operation 304 to one or more predetermined stability criteria, illustrated by the stable period determination operation 306. The comparison may include comparing data from a fixed "window" or period of time to the stability criteria. For example, in an embodiment, a fixed window (i.e., a window of 50 milliseconds (ms) of data or of ten consecutive measurement obtained from the sensors) of the most recent data may be compared to the stability criteria.

The stability criteria are selected specifically to identify such stable periods during which the patient is neither breathing in nor breathing out significantly. In an embodiment, the stability criteria may include static criteria (e.g., a predetermined threshold that remains fixed based on operator selected settings such as a positive end expiratory pressure (PEEP) level) and dynamic criteria that must be recalculated based on the current conditions as indicated by the data itself (e.g., a flow threshold that is a function of the amount of flow delivered up to that point in time). In addition, different stability criteria may be used depending on whether the current breath phrase is inhalation or exhalation.

Examples of stability criteria include a) a pressure based criterion such as a requirement that the average pressure during the window being evaluated is greater than a minimum pressure threshold or less than a maximum pressure threshold in which the threshold may be a static pressure based on the current ventilator settings or a dynamically generated pressure threshold based on current data; b) a pressure variation criterion identifying a maximum pressure variation within the window (e.g., a rate of change of pressure or a difference between pressure measurements within the window); c) a flow variation criterion identifying a maximum flow variation within the window; d) a mode criterion that verifies that a specific type of patient circuit, patient interface or ventilation mode is currently being used; e) a flow criterion identifying a minimum or maximum flow threshold; f) a time criterion identifying a minimum or maximum amount of time since some predefined event such as since the start of the current inhalation or exhalation cycle; and g) a volume criterion identifying a specific volume of gas that must have been inhaled or exhaled since the start of the current breath phase. As mentioned above, all of these criteria may be static criteria (unchanging during a breath) or may be dynamic criteria (that is criteria that recalculated based on current data either periodically or every time the stable period check is performed). Other types of criteria could also be used to identify stable periods including criteria based on patient effort as determined by ancillary equipment and criteria that are based on sensors other than pressure or flow sensors.

If the comparison of the data to the stability criteria indicates that the gas delivery by the ventilator does not meet the predetermined stability criteria, the conditions in the current window are not considered stable enough to use in determining the current leakage of the system. In this case, the determination operation 306 branches to an estimate instantaneous leakage operation 310 in which the instantaneous leakage from the ventilation tubing system is calculated using previously determined leakage information, that is leakage information gathered prior to the comparison, such as during a previous breath, set of breaths or stable period.

The estimate instantaneous leakage operation 310 may calculate the instantaneous leakage using any one (or more) of known leakage modeling techniques. These include calculating an instantaneous leak using an algorithm that estimates instantaneous leakage based on the current (or instantaneous) pressure within the system and some predetermined leakage information, such as a leak conductance, a leak factor or one or more hypothetical orifice constants. For example, in one embodiment, the instantaneous leakage is modeled as a hypothetical rigid orifice in which the instantaneous leakage from the system is simply a function of a predetermined orifice constant and the square root of the instantaneous pressure. In another embodiment, a leak conductance may be calculated and the instantaneous leakage from the system is a function of a predetermined conductance and the square root of the instantaneous pressure. In yet another embodiment, a leak factor may be calculated and the instantaneous leakage from the system is a function of a predetermined leak factor and the instantaneous pressure or some other parameter indicative of the current operation of the system. In yet another embodiment, the instantaneous leakage may be modeled as a set of different hypothetical orifices each representing different aspects of leakage (e.g., a rigid orifice of constant size and one or more dynamic orifices that change in size based on instantaneous pressure) in which the instantaneous leakage from the system is a function of the predetermined orifice constant for each orifice and the instantaneous pressure. Any suitable leakage model may be used in the estimate instantaneous leakage operation 310 now known or later developed.

However, if the comparison of the data to the stability criteria indicates that the window of data meets the predetermined stability criteria, the window is considered stable and the patient is assumed to not be inhaling or exhaling. In this case, the determination operation 306 branches to an update leakage information operation 308.

In the update leakage information operation 308, the data from the time period of the stable window is used to generate leakage information from which the instantaneous leakage may be determined. The type of leakage information generated is determined by the leakage model used in the estimate instantaneous leakage operation 310. As discussed above, any suitable leakage model may be used in the estimate instantaneous leakage operation 310 now known or later developed. However, it is presumed that each leakage model will require some type of predetermined leakage information in order to estimate instantaneous leakage at any particular moment from a current pressure measurement. This leakage information may take the form of one or more orifice constants, leak conductances, leak factors, exponents, or other leak characteristics as required by a leakage model.

The term leakage information, as used herein, refers to any such predetermined information that is later used in to estimate instantaneous leakage from the system based on the current system's conditions. The leakage information differs from prior art systems in that it is calculated from data taken during a narrow window of time that is entirely within a breath. In an embodiment, windows are limited a fixed duration within either the exhalation or inhalation phase of a breath so that no window will span time within two phases. In an alternative embodiment, depending on the stability criteria used embodiments of the leakage determining systems and methods described herein may or may not require identification of whether the patient is in an inhalation or exhalation phase. Note that because the onset of either phase of a breath will exhibit significant instability in that the pressure and/or flow will be changing, appropriate selection of length of the window to be analyzed and the stability criteria will prevent the possibility that of a window being identified as stable when it straddles two phases.

The update leakage information operation 308 uses some or all of the data from the identified stable window of time to calculate new leakage information. This new leakage information may then be used instead of the previously calculated leakage information or may be used in conjunction with some or all of the previously calculated leakage information. For example, in an embodiment in which a multiple orifice model is used to model the leakage from the ventilation tubing system, one or more of the orifice constants may be updated (i.e., changed based on the data within the window) while other constants used in the model may be retained from earlier calculations.

In an embodiment, the update leakage information operation 308 may update the leakage information to one or more default values based on the data in the stable window instead of calculating new values from the data. For example, if the data in the stable window indicates that the leakage during the time period of the stable window was very low, the leakage information may be set to some default minimum value. Likewise, if the data in the stable window indicates that the leakage during the time period of the stable window was very high, the leakage information may be set to some default maximum value.

After the leakage information operation 308 has updated some or all of the leakage information based on the data from the stable window, in the embodiment shown the estimate instantaneous leakage information 310 is performed. In an embodiment, this may be performed in the same computational cycle that the leakage information is updated. Alternatively, this may be performed in a later cycle, wherein the current instantaneous leakage information is obtained from a different method. For example, in a dual-limb ventilation system during a stable period the estimated instantaneous leakage may be discarded in favor of the direct measurement of the leakage, i.e., the difference between the measured inflow into the inspiratory limb and the measured outflow out of the expiratory limb.

The method 300 also compensates the delivery of respiratory gas based on the instantaneous leakage, as illustrated by the compensate operation 312. As discussed above, this may include compensating a lung flow estimate for instantaneous leakage or changing the amount of gas delivered to the inspiratory limb in order to compensate for the estimated instantaneous leakage. Other compensation actions may also be performed.

The method 300 then repeats so that the ventilator is continuously monitoring the delivery of gas to identify stable periods within a breath phase and update the leakage information based on the data from those stable periods. In an embodiment, additional leakage information may be determined at specified points in the respiratory cycle. For example, in an embodiment leakage information may be determined at the end of every breath for use in the next breath. The method 300 may then be used in order to cheek the leakage information determined at the end of a breath. This embodiment is described in greater detail with reference to FIG. 4.

Figure 4:
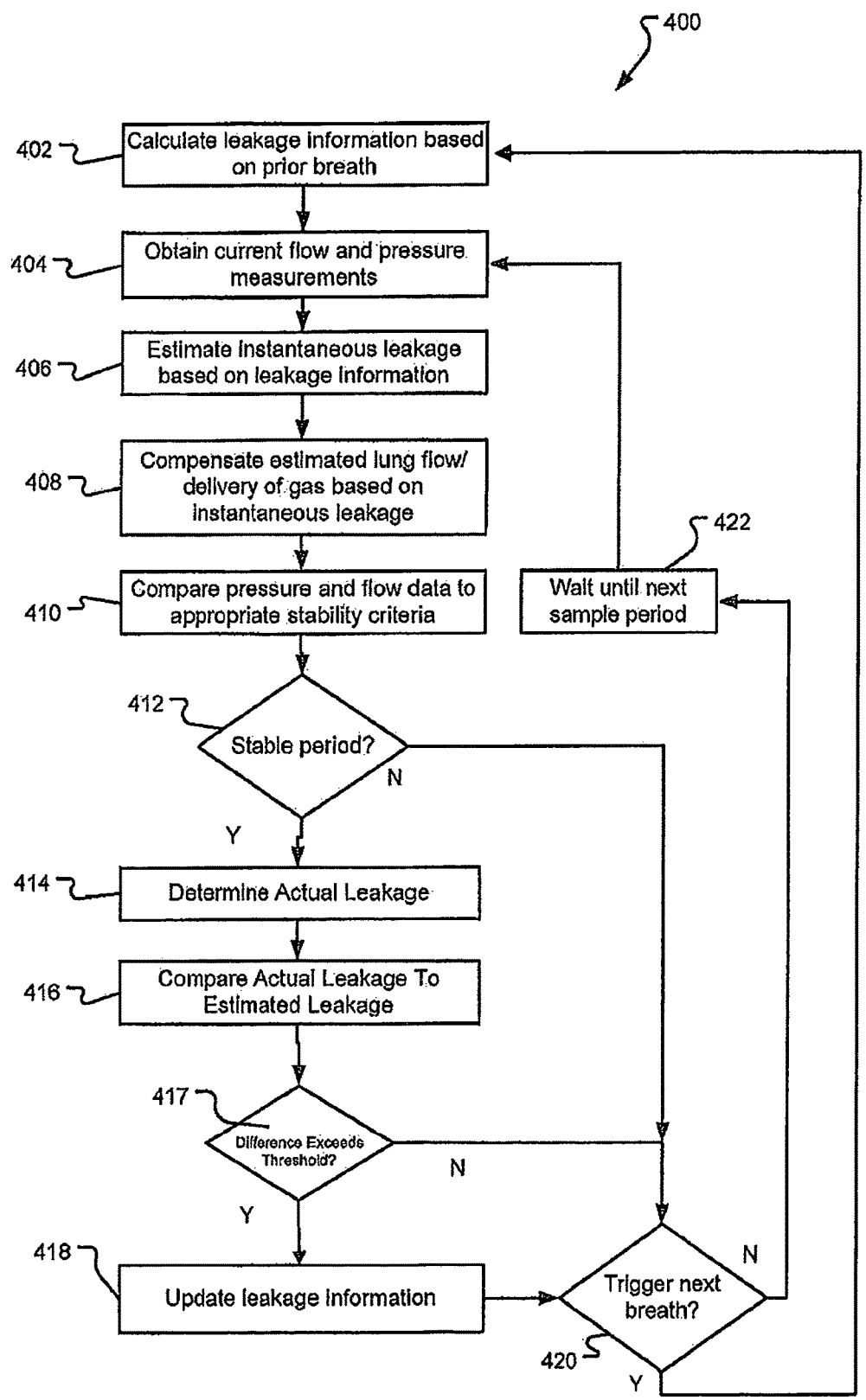
FIG. 4 illustrates another embodiment of a method for identifying the leakage from a ventilation tubing system of a respiratory gas supply system.

FIG. 4 illustrates another embodiment of a method for identifying the leakage from a ventilation tubing system of a respiratory gas supply system. In the embodiment shown, a ventilator such any of those described above is delivering gas to a patient. Again, the patient may be initiating breaths on his/her own (i.e., actively breathing) or the delivery of gas may be completely controlled by the ventilator so that respiratory gas is forced into and out of the lungs of the patient without any action on the patient's part.

In the method 400, at the beginning of each new breath, leakage information is calculated from data taken during one or more prior breaths in a calculate leakage information operation 402. Unless changed by the later update leakage operation 418 (discussed below) this leakage information will be used in the estimate instantaneous leakage operation 406 for the remainder of the breath; this will occur, for instance, if no stable periods are identified during the breath.

In the embodiment shown, the remaining operations in the method 400, i.e., operations 404-422, are repeated until the next breath is triggered. During this time, the ventilator is providing ventilatory support to the patient as directed by a caregiver.

The method 400 includes obtaining the current flow and pressure measurements from the various sensors in the ventilator in an obtain data operation 404.

An estimate instantaneous leakage operation 404 is then performed as described above with reference to the estimate instantaneous leakage operation 310 in FIG. 3. This operation 404 calculates an instantaneous leakage based on the current pressure measurements (and/or other data depending on the leakage model used).

The ventilator then compensates for the estimated instantaneous leakage in a compensate operation 408 as described above with reference to the compensate operation 312 in FIG. 3.

The method 400 also performs a comparison of the data obtained in the obtain data operation 404 as illustrated by the compare data operation 410. The compare data operation 410 compares data from a recent window of time in order to identify a stable period as described above with reference to FIG. 3. The comparison may include comparing a fixed window of data to the stability criteria. For example, in an embodiment, a fixed window (i.e., a window of 50 milliseconds (ms) of data or of ten consecutive measurement obtained from the sensors) of the most recent data including the current data may be compared to the stability criteria.

If the compare data operation 410 determines that the window being analyzed is not sufficiently stable (i.e., it does not meet the predetermined stability criteria) as determined by a first determination operation 412, the current leakage information is not updated and another determination operation 420 is performed to determine if a new breath should be triggered or not and the method 400 then repeats as shown.

If the compare data operation 410 determines that the window being analyzed contains data that are sufficiently stable (i.e., the data in the window meet the predetermined stability criteria) as determined by the first determination operation 412, operations 414-418 are performed to check the accuracy of the current leakage information to determine if some or all of that information should be updated based on the data in the stable window.

The accuracy cheek includes a determine actual leakage operation 414 in which the actual leakage during the stable window is determined based on known information and data obtained from the stable window. In a dual-limb embodiment, this may include calculating the difference between the measured inflow into the inspiratory limb and the measured outflow from the expiratory limb. In a single-limb embodiment, this may include calculating the difference between the measured inflow into the inspiratory limb and a measured or otherwise known exhaust(s) from the limb and/or patient interface. For example, the exhaust from an exhaust port in a patient interface may be monitored or otherwise determinable based on a known size or known features of the exhaust port and the current conditions. The actual leakage may be an average leakage rate during the window, a total leakage volume that leaked out during some or all of the window, or some other element of information that describes the leakage during or within the stable window.

The actual leakage during the window is then compared in a second compare operation 416 to the estimated leakage previously determined in the estimate leakage operation 406. If the actual leakage does not differ from the estimated leakage by more than a threshold amount, as illustrated by determination operation 417, the current leakage information is not updated and another determination operation 420 is performed to determine if a new breath should be triggered or not. However, if the actual leakage differs from the estimated leakage by more than a threshold amount an update leakage information operation 418 is performed.

The update leakage information operation 418 updates some or all of the leakage information as described above with reference to the update leakage information operation 308 in FIG. 3.

Figure 5:
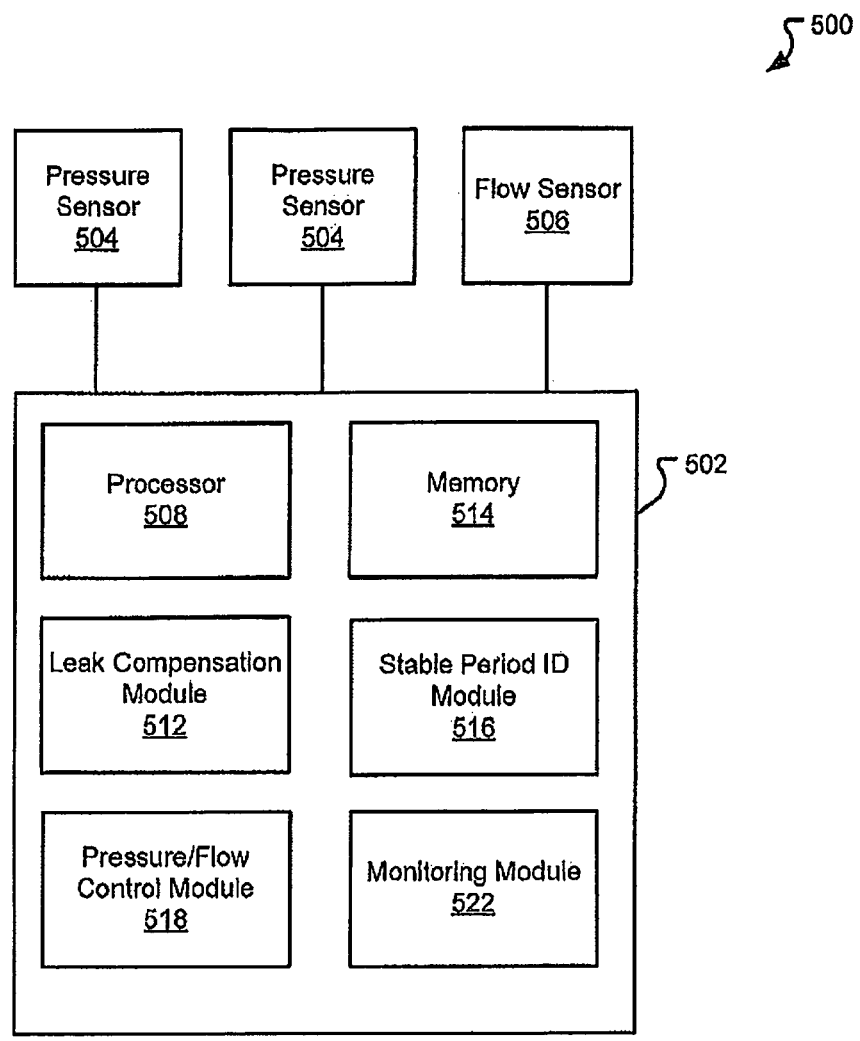
FIG. 5 illustrates a functional block diagram of modules and other components that may be used in an embodiment of ventilator that compensates for leaks.

FIG. 5 illustrates a functional block diagram of modules and other components that may be used in an embodiment of ventilator that compensates for leaks. In the embodiment shown, the ventilator 500 includes pressure sensors 504 (two are shown placed at different locations in the system), flow sensors (one is shown), and a ventilator control system 502. The ventilator control system 502 controls the operation of the ventilator and includes a plurality of modules described by their function. In the embodiment shown, the ventilator control system 502 includes a processor 508, memory 514 which may include mass storage as described above, a leak compensation module 512 incorporating at least one leak model such as that described in commonly-owned U.S. Provisional Application 61/041,070 hereby incorporated herein, a stable period identification module 516, a pressure and flow control module 518, and a monitoring module 522. The processor 508 and memory 514 have been discussed above. Each of the other modules will be discussed in turn below.

The main functions of the ventilator such as receiving and interpreting operator inputs and changing pressure and flow of gas in the ventilator circuit are performed by the control module 518. In the context of the methods and systems described herein, the module 518 may perform one or more actions upon the determination that a patient receiving therapy is inhaling or exhaling.

The current conditions in the ventilation system are monitored by the monitoring module 522. This module 522 collects the data generated by the sensors 504, 506 and may also perform certain calculations on the data to make the data more readily usable by other modules or may process the current data and or previously acquired data or operator input to derive auxiliary parameters or attributes of interest. In an embodiment, the monitoring module 522 receives data and provides it to each of the other modules in the ventilator control system 502 that need the current pressure or flow data for the system.

The ventilator 500 further includes a stable period identification module 516. The stable period identification module 516 analyzes data obtained by the monitoring module 522 in order to identify periods of stability within a breath during which the patient is neither inhaling nor exhaling. The methods discussed above describe various embodiments for identifying stable periods using dynamic and/or static stability criteria. Other embodiments are also possible and any method that can accurately identify a stable period may be used.

When a stable period is identified, this information is passed to the leak compensation module 512. The leak compensation module 512 may then update the current leak information to leak information derived from the stable period. In an embodiment, the leak compensation module 512 may first compare the actual leakage during the stable period to the amount of leakage estimated for the period using the current leakage information. The results of this comparison may then dictate whether and how the current leakage information is updated by leakage information calculated from the data taken during the stable period.

In the embodiment shown, the current or instantaneous inelastic leak is also calculated by the leak compensation module 512 using one or more predetermined leakage models. The leak compensation module 512 may estimate a new instantaneous flow or volume for each sampling period using data taken by the monitoring module 522. The estimated instantaneous leak may then be provided to any other module as needed.

In an embodiment, the leak compensation module 512 uses the two orifice leak compensation model described in U.S. Provisional Application 61/041,070 which is provided as an attachment hereto and which forms a part of this application. In this embodiment, the leak compensation module 512 calculates leakage information that includes the orifice constant $K_1$ which represents leakage through an orifice of fixed size and the orifice constant $K_2$ which represents a dynamic orifice that changes size in response to changes in pressure. After calculating the leakage information, the leak compensation module 512 then uses the following equation to calculate instantaneous leakage at later points in time:

$$\text{Instantaneous Leakage} = K_1 P^{0.5} + K_2 P^{1.5}$$

in which P is the instantaneous pressure. During a stability check, if it is determined that the leakage information should be changed, either the $K_1$ or the $K_2$ or both constants may be changed.

In addition, in the embodiment shown the leak compensation module 512 also is responsible for compensating for the estimated instantaneous leakage. This may include compensation the estimates of other parameters such as lung flow and may include providing information to the control module 518 to change the pressure or flow of the delivery of gas to the patient.

The system 500 illustrated will perform a dynamic compensation of lung flow based on the changing leak conditions of the ventilation system and the instantaneous pressure and flow measurements. By identifying stable periods within a breath from which accurate leakage information may be determined, the medical ventilator can more quickly, accurately and precisely identify changes the leakage from the ventilation tubing system and control the delivery of gas to compensate for such changes in leakage.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. In other words, functional elements being performed by a single or multiple components, in various combinations of hardware and software, and individual functions can be distributed among software applications at either the client or server level. In this regard, any number of the features of the different embodiments described herein may be combined into one single embodiment and alternate embodiments having fewer than or more than all of the features herein described are possible. For example, the various operations in the embodiments of methods described above may be combined or reordered as desired without deviating from the overall teaching of this disclosure.

While various embodiments have been described for purposes of this disclosure, various changes and modifications may be made which are well within the scope of the present invention. For example, leak information need not be calculated in real time for immediate use in determining instantaneous leakage. In an embodiment, leak information from one or more stable periods during a breath phase may be calculated and/or used after that breath in calculating instantaneous leakage during one or more subsequent breaths.

Numerous other changes may be made which will readily suggest themselves to those skilled in the art and which are encompassed in the spirit of the disclosure and as defined in the appended claims.

What is claimed is:

1. A method for identifying leakage in a respiratory gas supply system, the respiratory gas supply system having a controller adapted for delivering a flow of respiratory gases to a breathing patient, the method comprising:
    monitoring data indicative of at least one of pressure and flow in the respiratory gas supply system;

identifying, by the controller, that the data meet at least one stability criterion indicating that pressure and flow conditions have been stable for a period of time within a breath of a patient;

in response to the identifying that the data meet the at least one stability criterion, calculating leakage information based at least in part on the data identified during the period of time within the breath;

determining, by the controller, a leakage rate after the period of time based at least in part on the leakage information; and adjusting at least one of a pressure and a flow delivered to the patient based on the determined leakage rate.

2. The method of claim 1 further comprising:
displaying the leakage rate to a user on a display.

3. The method of claim 1 wherein determining a leakage rate further comprises:
determining an instantaneous leakage rate after the period of time using only the leakage information and a pressure measurement taken after the period of time.

4. The method of claim 1 wherein determining a leakage rate further comprises:
determining an instantaneous leakage rate after the period of time using the leakage information and at least one current pressure measurement in the respiratory gas supply system.

5. The method of claim 1 further comprising:
monitoring data indicative of pressure at two different locations in a patient circuit.

6. The method of claim 1 further comprising:
monitoring data indicative of flow at two different locations in the patient circuit.

7. The method of claim 1 further comprising:
monitoring data indicative of at least one of pressure and flow at different locations in the patient circuit.

8. The method of claim 1 wherein calculating leakage information comprises:
calculating at least one constant based on data taken during the period of time, wherein the constant relates pressure to leakage rate in the respiratory gas supply system.

9. The method of claim 1 wherein calculating leakage information comprises:
calculating a first orifice constant representing the relationship between leakage flow through a hypothetical orifice and pressure in the respiratory gas supply system based on data taken during the period of time.

10. The method of claim 1 wherein identifying further comprises:
periodically analyzing, while providing therapy to a patient, a window of the data, wherein the window comprises recently monitored data, and wherein the periodic analyzing is performed to determine whether the window of the data meets the at least one stability criterion.

11. The method of claim 1 wherein identifying comprises:
calculating a first value indicative of a rate of change of pressure during at least a portion of the period of time;
comparing the first value to a first stability criterion; and
based at least in part on a result of the comparing of the first value to the first stability criterion, classifying the period of time as stable.

12. The method of claim 11 wherein identifying comprises:
calculating a second value indicative of a rate of change of flow during at least a portion of the period of time;
comparing the second value to a second stability criterion; and
based at least in part on a result of the comparing the second value, classifying the period of time as stable.

13. A respiratory gas supply system comprising:
a pressure generating system configured to control flow of breathing gas through a patient circuit and a patient interface to a patient; and
a computer controller communicatively coupled to the pressure generating system for adjusting the flow of breathing gas delivered to the patient, the computer controller configured to:
identify a stable period within at least one of an inhalation phase and an exhalation phase of a breath;
calculate leakage information using data obtained during the stable period identified by the stable period identification module;
calculate, during unstable periods within the breath or a later breath, an instantaneous leakage rate based on the leakage information; and
adjust at least one of a pressure and a flow delivered to the patient based on the determined leakage rate.

14. The respiratory gas supply system of claim 13, wherein identifying the stable period comprises comparing a window of recent pressure and flow data to a first set of one or more stability criteria during the inhalation phase.

15. The respiratory gas supply system of claim 14 wherein the first set of one or more stability criteria includes at least one criterion selection from a first criterion identifying a minimum pressure, a second criterion identifying a maximum pressure variation within the window, a third criterion identifying a maximum flow variation within the window and a fourth criterion based on a patient circuit type.

16. The respiratory gas supply system of claim 13 wherein identifying the stable period comprises comparing the window of recent pressure and flow data to a second set of one or more stability criteria during the exhalation phase.

17. The respiratory gas supply system of claim 16 wherein the second set of one or more stability criteria includes at least one criterion selected from a fifth criterion identifying a pressure threshold, a sixth criterion identifying a minimum time since the patient began to exhale, a seventh criterion identifying a minimum flow, an eighth criterion identifying a maximum pressure variation within the window and a ninth criterion identifying a maximum flow variation within the window.

18. A method for determining leakage from a respiratory gas supply system, the respiratory gas supply system having a controller adapted for providing respiratory gases to a breathing patient, comprising:
identifying, by the controller, at least one stable period within a breath of a patient;
calculating leakage information from pressure and flow data obtained during the at least one stable period;
subsequent to the at least one stable period, estimating, by the controller, a leakage from the respiratory gas supply system based on the leakage information and current data; and
adjusting at least one of a pressure and a flow delivered to the patient based on the determined leakage.

19. The method of claim 18 wherein calculating leakage information further comprises:
calculating a net leakage from the respiratory gas supply system during the at least one stable period based on measurements of respiratory gas flow to the patient and respiratory gas flow exiting the respiratory gas supply system.

20. The method of claim 18 wherein calculating leakage information further comprises:
  calculating a representative pressure in the respiratory gas supply system during the at least one stable period based on measurements of pressure.

21. The method of claim 18 wherein calculating leakage information further comprises:
  determining leakage information based on the net leakage from the respiratory gas supply system and the representative pressure.

22. The method of claim 20 wherein calculating a representative pressure comprises:
  calculating a square root of an average pressure in the respiratory gas supply system during the at least one stable period.

* * * * *